US011464999B2

(12) United States Patent
Liu

(10) Patent No.: US 11,464,999 B2
(45) Date of Patent: Oct. 11, 2022

(54) COLLIMATING BODY AND MULTI-SOURCE FOCUSING RADIATION THERAPY HEAD

(71) Applicant: OUR UNITED CORPORATION, Shaanxi (CN)

(72) Inventor: Haifeng Liu, Shaanxi (CN)

(73) Assignee: OUR UNITED CORPORATION, Shaanxi (CN)

( * ) Notice: Subject to any disclaimer, the term of this patent is extended or adjusted under 35 U.S.C. 154(b) by 364 days.

(21) Appl. No.: 16/618,141

(22) PCT Filed: Apr. 26, 2018

(86) PCT No.: PCT/CN2018/084648
§ 371 (c)(1),
(2) Date: Nov. 28, 2019

(87) PCT Pub. No.: WO2018/219077
PCT Pub. Date: Dec. 6, 2018

(65) Prior Publication Data
US 2020/0164228 A1 May 28, 2020

(30) Foreign Application Priority Data
May 31, 2017 (CN) .......................... 201720620521.6

(51) Int. Cl.
*A61N 5/10* (2006.01)
*G21K 1/02* (2006.01)
*G21K 1/04* (2006.01)

(52) U.S. Cl.
CPC .......... *A61N 5/1042* (2013.01); *G21K 1/025* (2013.01); *G21K 1/04* (2013.01)

(58) Field of Classification Search
CPC .......... G21K 1/04; G21K 1/043; G21K 1/046
USPC ....................... 378/147, 148, 149; 250/363.1
See application file for complete search history.

(56) References Cited

FOREIGN PATENT DOCUMENTS

| CN | 105708484 A | 6/2016 | |
|---|---|---|---|
| CN | 105727449 A | 7/2016 | |
| CN | 106334274 A | 1/2017 | |
| JP | 2010068908 A | 4/2010 | |
| WO | WO-2003047695 A1 | 6/2003 | |
| WO | WO-2015176265 A1 * | 11/2015 | ............... G21K 5/04 |

OTHER PUBLICATIONS

International Search Report and Written Opinion for Application No. PCT/CN2018/084648 dated Jul. 17, 2018.

* cited by examiner

*Primary Examiner* — Kaylee R Wilson
(74) *Attorney, Agent, or Firm* — Marshall, Gerstein & Borun LLP

(57) ABSTRACT

The present disclosure provides a collimating body and a multi-source focusing radiation therapy head. The collimating body includes a first collimating portion and a second collimating portion. The first collimating portion and the second collimating portion are arranged side by side and closely fixed. The first collimating portion includes a first collimating hole set, and the second collimating portion includes a second collimating hole set. The first collimating portion and the second collimating portion are able to move oppositely in a direction perpendicular to a side-by-side direction, so as to align or stagger the first collimating hole set and the second collimating hole set.

15 Claims, 4 Drawing Sheets

COLLIMATING BODY AND MULTI-SOURCE FOCUSING RADIATION THERAPY HEAD

CROSS-REFERENCE TO RELATED APPLICATION

This application is a national phase entry under 35 USC 371 of International Patent Application No. PCT/CN2018/084648 filed on Apr. 26, 2018, which claims priority to Chinese Patent Application No. 201720620521.6 filed on May 31, 2017, which are incorporated herein by reference in their entirety.

TECHNICAL FIELD

The present disclosure relates to the field of radiation therapy instruments, and in particular, to a collimating body and a multi-source focusing radiation therapy head.

BACKGROUND

Radiation therapy, as a means of cancer treatment, is currently widely used in medicine. A multi-source focusing radiation therapy, one of the radiation therapy technologies, integrates modern computer technologies, stereotactic technologies and surgeries, which may geometrically focus the rays emitted by the radioactive source, concentrate on niduses, and destroy the tissue within the target in a one-time and lethal manner, while the rays pass through normal human tissue with little damage.

The existing multi-source focusing radiation therapy equipment includes a roller, a treatment head and a treatment bed. The treatment head is mounted on the roller, and the roller drives the treatment head to rotate around a focus. The treatment bed is located on a side of the roller in an axial direction, and the treatment bed may move along the roller in the axial direction through the center opening of the roller. The treatment head sequentially includes a shielding body, a source body and a collimating body from the outside to the inside, and the shielding body is located outside the source body for shielding radiation of the radioactive source to the external environment. The source body is provided with a plurality of carrier chambers and ray through-holes, and the carrier chambers are used for loading the radioactive source. The collimating body is provided with a plurality of conical collimating holes for focusing beams emitted by the radioactive source. During treatment, the collimating holes on the collimating body are aligned with the ray through-holes on the source body, and ray beams emitted by the radioactive source in the source body pass through the ray through-holes and the collimating holes and converge to the focus to treat the affected regions of the patient on the treatment bed.

Since the shapes of the affected regions of the patient are often irregular, the affected regions in different positions require different sizes and shapes of the radiation field. During the treatment, for the treatment of different affected regions, the collimating bodies having different aperture sizes need to be changed, which makes the treatment process complicated. In order to simplify this process, a plurality of the collimating holes having different aperture sizes are disposed on one collimating body, and the collimating body is moved to match the collimating holes having different aperture sizes according to the treatment needs.

With the improvement of precision requirements of modern radiation therapy technologies, not only the accuracy of the shape of the radiation field projected onto the tumor is required, but also the accuracy of the radiation doses projected onto the tumor is required. It is difficult to satisfy the requirement of high accuracy treatment by using the existing collimating bodies having a plurality of the collimating holes with different aperture sizes because of the single shape of the radiation field and low control accuracy of dose rates.

Therefore, how to provide a collimating body and a multi-source focusing radiation therapy head that may adjust the shapes of the radiation field and improve the accuracy of the dose control at the focus becomes an urgent problem to be solved in the art.

SUMMARY

The purpose of the present disclosure is to provide a collimating body and a multi-source focusing radiation therapy head that may adjust a shape of the radiation field at the focus, increase a dose control range and improve accuracy of the dose control.

The purpose of the present disclosure is achieved by the following technical solutions.

A collimating body includes a first collimating portion, and the first collimating portion includes a first collimating hole set; a second collimating portion, and the second collimating portion includes a second collimating hole set; the first collimating portion and the second collimating portion are arranged side by side in a side-by-side direction and closely fitted; the first collimating portion and the second collimating portion are able to move oppositely in a direction perpendicular to the side-by-side direction, so as to align or stagger the first collimating hole set and the second collimating hole set.

Preferably, the first collimating portion includes at least one first collimating hole set; the second collimating portion includes a plurality of second collimating hole sets, and the plurality of second collimating hole sets are distributed in the direction perpendicular to the side-by-side direction; at least one of the plurality of second collimating hole sets is configured in a way that an aperture size of each second collimating hole in the at least one of the plurality of second collimating hole sets is not completely equal to an aperture size of each second collimating hole in other second collimating hole sets.

Preferably, the second collimating portion includes at least one second collimating hole set; the first collimating portion includes a plurality of first collimating hole sets, and the plurality of first collimating hole sets are distributed in the direction perpendicular to the side-by-side direction; at least one of the plurality of first collimating hole sets is configured in a way that an aperture size of each first collimating hole in the at least one of the plurality of first collimating hole sets is not completely equal to an aperture size of each first collimating hole in other first collimating hole sets.

Preferably, the first collimating portion includes a plurality of first collimating hole sets, and an aperture sizes of each of the plurality of first collimating hole sets is not completely equal to each other; the second collimating portion includes a plurality of second collimating hole sets, and an aperture sizes of each of the plurality of second collimating hole sets is not completely equal to each other.

Preferably, the number of the first collimating hole sets included in the first collimating portion is equal to the number of the second collimating hole sets included in the second collimating portion.

Preferably, the first collimating hole set includes a plurality of first collimating holes having a same aperture size, and the second collimating hole set includes a plurality of second collimating holes having a same aperture size.

Preferably, the first collimating hole set includes a plurality of first collimating holes with aperture sizes which are not completely equal to each other, and the second collimating hole set includes a plurality of second collimating holes with aperture sizes which are not completely equal to each other.

Preferably, the number of the first collimating holes included in each first collimating hole set is equal to the number of the second collimating holes included in each second collimating hole set.

Preferably, the number of the first collimating holes included in each first collimating hole set is different from the number of the second collimating holes included in each second collimating hole set.

Preferably, the first collimating portion includes a plurality of first collimating hole sets, and the second collimating portion includes a plurality of second collimating hole sets, and an aperture size of each of the plurality of first collimating hole sets is equal to an aperture size of each of the plurality of second collimating hole sets in one-to-one correspondence.

Preferably, the collimating body further includes a first driving portion, and the first driving portion is configured to drive the first collimating portion to move in the direction perpendicular to the side-by-side direction relative to the second collimating portion.

Preferably, the collimating body further includes a first brake portion, and the first brake portion is configured to limit a movement of the first driving portion.

Preferably, the collimating body further includes a second driving portion, and the second driving portion is configured to drive the second collimating portion to move in the direction perpendicular to the side-by-side direction relative to the first collimating portion.

Preferably, the collimating body further includes a second brake portion, and the second brake portion is configured to limit a movement of the second driving portion.

Preferably, the first collimating portion includes a first stepped portion, and the second collimating portion includes a second stepped portion that cooperates with the first stepped portion.

A multi-source focusing radiation therapy head includes any one of the above collimating bodies.

A collimating body of the present disclosure includes the first collimating portion and the second collimating portion. The first collimating portion and the second collimating portion are arranged side by side in the side-by-side direction and closely fixed. The first collimating portion includes a first collimating hole set, and the second collimating portion includes a second collimating hole set. The first collimating portion and the second collimating portion may be oppositely moved in the direction perpendicular to the side-by-side direction, so as to align or stagger the first collimating hole set and the second collimating hole set. In this manner, relative positions of the first collimating portion and the second collimating portion may be adjusted in the direction perpendicular to the side-by-side direction, so as to adjust relative positions of the first collimating hole sets and the second collimating hole sets, realize different combinations of the first collimating hole sets and the second collimating hole sets, adjust shapes and sizes of the radiation field, provide more kinds of shapes of the radiation field, and increase a dose control range at the focus and improve an accuracy of the dose control.

DETAILED DESCRIPTION

Figure 1:
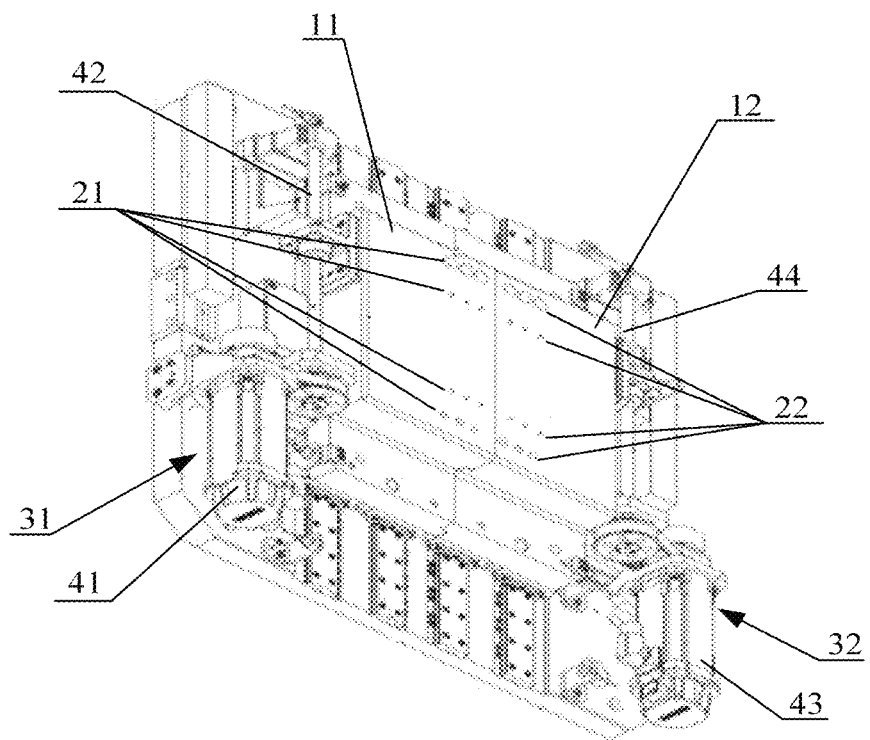
FIG. 1 is a schematic diagram of a collimating body, according to some embodiments of the present disclosure.

In the description of the present disclosure, it will be understood that the orientation or positional relationship indicated by the terms "center", "lateral", "upper", "lower", "left", "right", "vertical", "horizontal", "top", "bottom", "inner", "outer" and so on are based on the orientation or positional relationship shown in the drawings, and is merely for the convenience of description of the present disclosure and the simplification of the description, rather than indicate or imply that the device or component referred to must have a particular orientation, configuration and operation in a particular orientation, and thus cannot be construed as the limitation of the present disclosure. Moreover, the terms "first" and "second" are only used for describing purpose, and are not to be construed as indicating or implying a relative importance or implicitly indicating the number of indicated technical features. Thus, the features defined with "first" and "second" may explicitly or implicitly include one or more of the features. In the description of the present disclosure, the term "a plurality of" means two or more than two, unless specified otherwise. Additionally, the terms "comprising", "including", and any deformation thereof are intended to cover a non-exclusive inclusion.

In the description of the present disclosure, unless specified or defined otherwise, it will be noted that the terms "mounted", "connected", "coupled" should be understood broadly, for example, a fixed connection, a detachable connection, or an integral connection; a mechanical or electrical connection; a direct connection or an indirect connection via intermediaries; an inner communication between two elements. The specific meanings of the above terms in the present disclosure can be understood by those ordinary skilled in the art according to specific situations.

The present disclosure will be further described in combination with the drawings and preferred embodiments.

Figure 2:
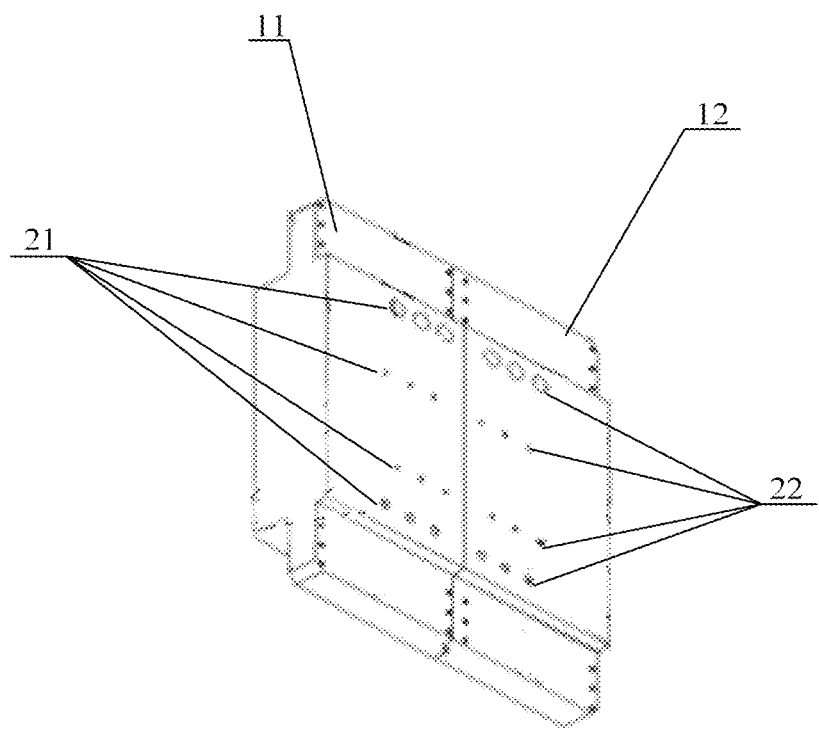
FIG. 2 is a partial structure diagram of a collimating body, according to some embodiments of the present disclosure.

As shown in FIG. 1 and FIG. 2, a collimating body is disclosed in this embodiment, including a first collimating portion 11 and a second collimating portion 12. The first collimating portion 11 and the second collimating portion 12 are arranged side by side in a side-by-side direction and closely attached. The first collimating portion 11 includes a first collimating hole set 21, and the second collimating portion 12 includes a second collimating hole set 22. The first collimating portion 11 and the second collimating portion 12 may be oppositely moved in a direction perpendicular to the side-by-side direction, so as to align or stagger the first collimating hole set 21 and the second collimating hole set 22.

In this manner, relative positions of the first collimating portion 11 and the second collimating portion 12 may be adjusted in the direction perpendicular to the side-by-side direction, so as to adjust relative positions of the first collimating hole set 21 and the second collimating hole set 22, realize different combinations of the first collimating hole set 21 and the second collimating hole set 22, adjust shapes and sizes of radiation field, provide more kinds of shapes of the radiation field, and increase a dose control range at a focus and improve an accuracy of the dose control.

The number of the first collimating hole sets 21 and the number of the second collimating hole sets 22 are not limited in the embodiment. The first collimating hole set 21 may be set as one set, and the second collimating hole set 22 may also be set as one set. Different shapes of the radiation field and dose adjustments may be realized by different combinations of first collimating hole sets and second collimating hole sets. Of course, the first collimating hole set 21 may be set as one set, and the second collimating hole set 22 may be set as two or more sets, so that the shape of the radiation field is more diverse. Of course, the second collimating hole set 22 may be set as one set and the first collimating hole set 21 may be set as two or more sets. It is also possible that the first collimating hole set 21 is set as two or more sets, and the second collimating hole set 22 is also set as two or more sets. The number of the first collimating hole sets 21 and the number of the second collimating hole sets 22 may be the same or different.

In the embodiment, each first collimating hole set may include one first collimating hole, and may also include two or more first collimating holes. Aperture sizes of the two or more first collimating holes may be the same or different. Each second collimating hole set may include one second collimating hole, and may also include two or more second collimating holes. Aperture sizes of the two or more second collimating holes may be the same or different. The number of the first collimating holes in the first collimating hole set may be the same as or different from the number of the second collimating holes in the second collimating hole set. Aperture sizes of the first collimating holes in the first collimating hole set may be the same as or different from aperture sizes of the second collimating holes in the second collimating hole set.

Figure 3:
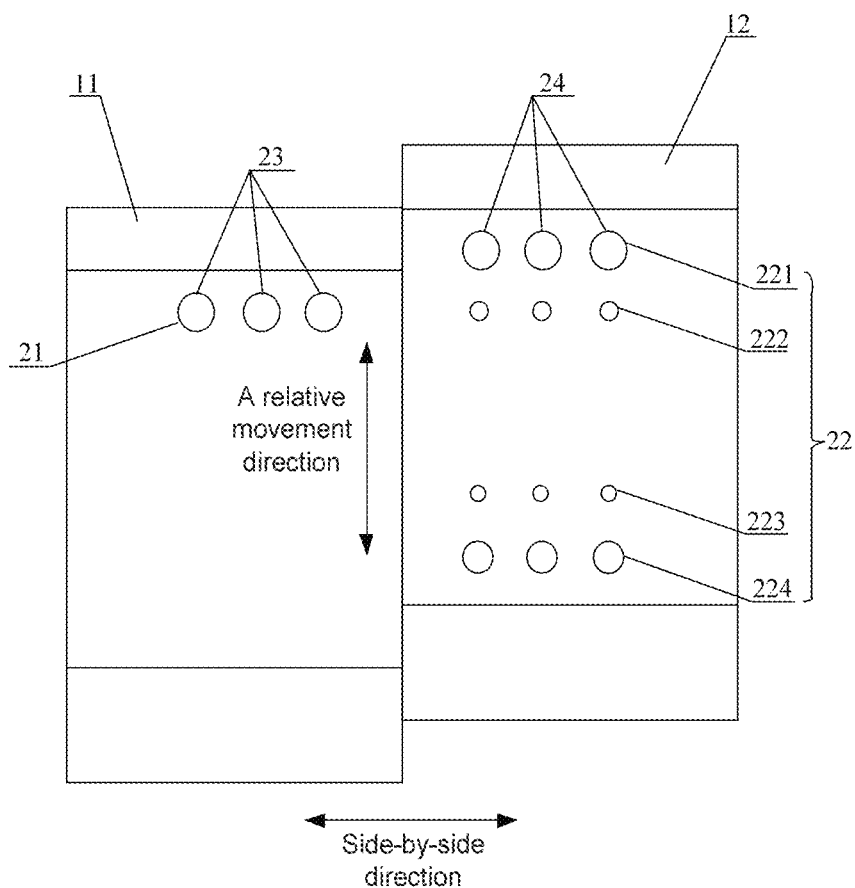
FIG. 3 is a partial top diagram of a collimating body, according to some embodiments of the present disclosure.

In the embodiment, for example, as shown in FIG. 3, the first collimating portion 11 includes one first collimating hole set 21 (FIG. 3 shows only part of structure of the first collimating portion 11. It should be understood that the first collimating portion 11 may include other numbers of first collimating hole sets, for example, two or three or five or more sets of first collimating hole sets); the second collimating portion 12 includes a plurality of second collimating hole sets 22, and the plurality of second collimating hole sets 22 are distributed in the direction perpendicular to the side-by-side direction. At least one of the plurality of second collimating hole sets 22 is configured in a way that an aperture size of each second collimating hole in the at least one of the plurality of second collimating hole sets is not completely equal to an aperture size of each second collimating hole in other second collimating hole sets. In this manner, an aperture size of each second collimating hole in the at least one of the plurality of second collimating hole sets 22 is not completely equal to an aperture size of each second collimating hole in other sets. Relative positions of the first collimating portion 11 and the second collimating portion 12 are adjusted in a relative movement direction shown in FIG. 3 to make the first collimating hole set 21 aligned side by side with the second collimating hole set 22 to form different shapes of the radiation field at the focus.

As shown in FIG. 3, the first collimating portion 11 includes one first collimating hole set 21. The first collimating hole set 21 includes three first collimating holes 23 arranged side by side, and aperture sizes of the three first collimating holes 23 are the same. The second collimating portion 12 includes four second collimating hole sets 22, which are arranged in four rows, including a first second collimating hole set 221, a second second collimating hole set 222, a third second collimating hole set 223 and a fourth second collimating hole set 224. Each second collimating hole set includes three second collimating holes, aperture sizes of the three second collimating holes in a same set are the same, and the four second collimating hole sets have different aperture sizes (in this case, the aperture size of the second collimating hole set is equal to an aperture size of each second collimating hole in the set). An aperture size of the first second collimating hole set 221 may be set as the largest, an aperture size of the third second collimating hole set 223 may be set as the smallest, and an aperture size of the second second collimating hole set 222 may be set as greater than the aperture size of the third second collimating hole set 223 but less than an aperture size of the fourth second collimating hole sets 224. In this way, the relative positions of the first collimating portion 11 and the second collimating portion 12 may be adjusted, so that the first collimating hole set 21 may be aligned with the first second collimating hole set 221, or may also be aligned with the second second collimating hole set 222, or may also be aligned with the third second collimating hole set 223, or may also be aligned with the fourth second collimating hole set 224, which may form different shapes and sizes of the radiation field by alignment of different second collimating hole sets and the first collimating hole set 21.

Figure 4:
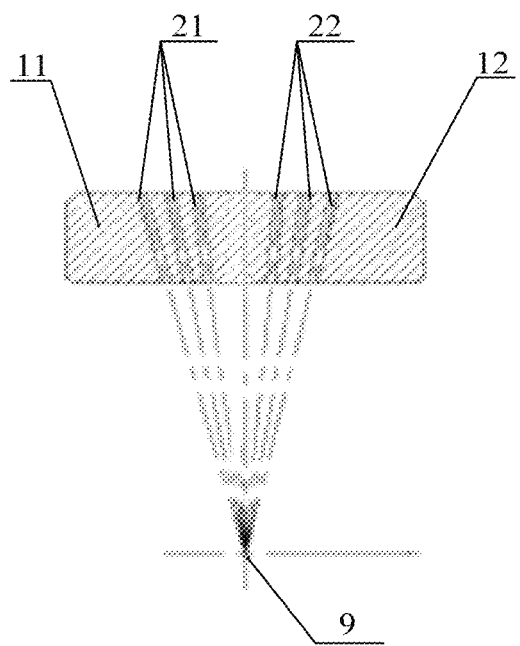
FIG. 4 is an operation schematic diagram of a collimating body, according to some embodiments of the present disclosure.

As shown in FIG. 4, in a case where the first collimating hole set 21 is aligned with one of the second collimating hole sets 22, ray beams emitted by six radioactive sources pass through the first collimating hole set 21 in the first collimating portion 11 and the second collimating hole sets 22 in the second collimating portion 12 to form two kinds of spots having different sizes. A combination of the two kinds of spots having different sizes may realize an adjustment of the shapes of the radiation field at the focus and an adjustment of a radiation dose at the focus. The ray beams are focused on the focus through the collimating holes. Since aperture sizes of the four second collimating hole sets 22 are different, the shapes and sizes of the radiation field formed at the focus may be adjusted, so as to obtain various shapes of the radiation field, and adjust the radiation dose at the focus more accurately. Of course, in the embodiment, the second collimating portion 12 may include two second collimating hole sets 22 having the same aperture sizes, as long as an aperture size of at least one of the second collimating hole sets 22 is different from aperture sizes of other second collimating hole sets 22, so as to achieve more various shapes and sizes of the radiation field. In the embodiment, the number of the first collimating holes in each first collimating hole set is not limited, and the number of the second collimating holes in each second collimating hole set is also not limited, and the above description is only an example.

Figure 5:
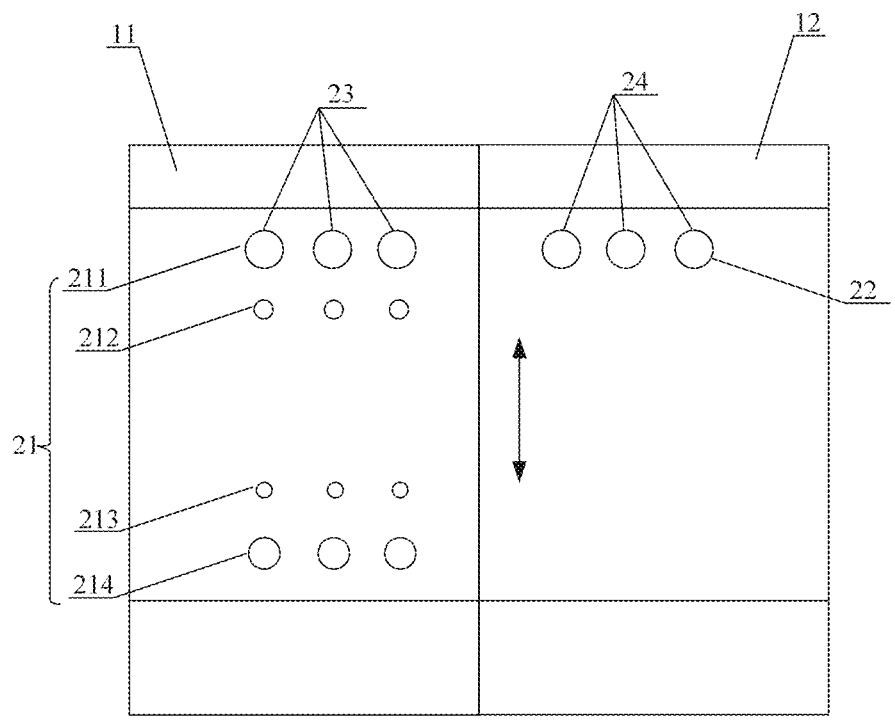
FIG. 5 is a partial top diagram of another collimating body, according to some embodiments of the present disclosure.

Exemplified in this embodiment, as shown in FIG. 5, the second collimating portion 12 includes one second collimating hole set 22 (FIG. 5 shows only part of structure of the second collimating portion 12. It should be understood that the second collimating portion 12 may include other numbers of second collimating hole sets, for example, two or three or five or more sets of second collimating hole sets). The first collimating portion 11 includes a plurality of first collimating hole sets 21, and the plurality of first collimating hole sets 21 are distributed in the direction perpendicular to the side-by-side direction. At least one of the plurality of first collimating hole sets 21 is configured in a way that an aperture size of each first collimating hole in the at least one of the plurality of the first collimating hole sets 21 is not completely equal to an aperture size of each first collimating hole in other first collimating hole sets 21. In this way, the second collimating hole sets 22 may be aligned with different first collimating hole sets 21 to form different shapes and sizes of the radiation field at the focus.

For example, as shown in FIG. 5, the first collimating portion 11 includes four first collimating hole sets 21, which are arranged in four rows, including a first first collimating hole set 211, a second first collimating hole set 212, a third first collimating hole set 213 and a fourth first collimating hole set 214. Each first collimating hole set 21 includes three first collimating holes 23, aperture sizes of the three second collimating holes in a same set are the same, and aperture sizes of the four first collimating hole sets 21 are different (in this case, the aperture size of the second collimating hole set is equal to an aperture size of each second collimating hole in the set). An aperture size of the first first collimating hole set 211 may be set as the largest, an aperture size of the third first collimating hole set 213 may be set as the smallest, and an aperture of the second first collimating hole set 212 may be set as greater than the aperture size of the third first collimating hole set 213 but less than an aperture size of the fourth first collimating hole set 214. The second collimating portion 12 includes one second collimating hole set 22, the second collimating hole set 22 includes three second collimating holes 24 arranged side by side, and aperture sizes of the three second collimating holes 24 are the same. In this way, the relative positions of the first collimating portion 11 and the second collimating portion 12 may be adjusted, so that the second collimating hole set 22 may be aligned with the four different first collimating hole sets 21. The second collimating hole set 22 may be aligned with the first first collimating hole set 211, or may also be aligned with the second first collimating hole set 212, or may also be aligned with the third first collimating hole set 213, or may also be aligned with the fourth first collimating hole set 214, and aperture sizes of the four first collimating hole sets are different, which may form different shapes and sizes of the radiation field by alignment of different first collimating hole sets and the second collimating hole set.

As shown in FIG. 4, in a case where the second collimating hole set 22 is aligned with one of the first collimating hole sets 21, rays are focused to a focus 9 through the collimating holes. Since the apertures sizes of the four first collimating hole sets 21 are different, the shapes and sizes of the radiation field formed at the focus may be adjusted, so as to obtain rich shapes of the radiation field, and the radiation dose at the focus may be adjusted more precisely. Of course, in the embodiment, the first collimating portion 11 may have two first collimating hole sets 21 having the same aperture size, as long as an aperture size of at least one of the first collimating hole sets 21 is different from aperture sizes of other first collimating hole sets 21, so as to achieve more various shapes and sizes of the radiation field. In the embodiment, the number of the second collimating holes in the second collimating hole sets is not limited, and the above is only an example. The number of the first collimating holes in each first collimating hole set is also not limited, and the above is only an example.

Figure 6:
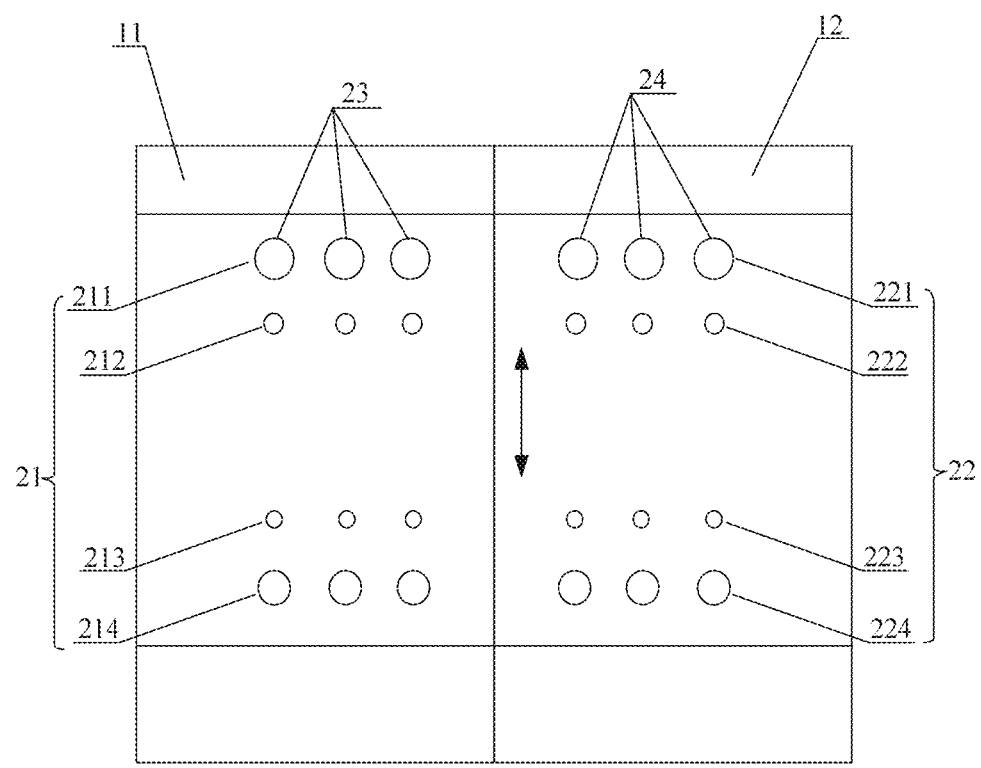
FIG. 6 is a partial top diagram of yet another collimating body, according to some embodiments of the present disclosure.

Exemplified in this embodiment, as shown in FIG. 6, the first collimating portion 11 includes a plurality of first collimating hole sets 21, an aperture size of each first collimating hole in each first collimating hole set 21 is the same, and aperture sizes of the plurality of first collimating hole sets 21 are not completely equal to each other. The second collimating portion 12 includes a plurality of second collimating hole sets 22, an aperture size of each second collimating hole in each second collimating hole set 21 is the same, and aperture sizes of the plurality of second collimating hole sets 22 are not completely equal to each other. In this manner, in a case where relative positions between the first collimating portion 11 and the second collimating portion 12 are adjusted, different first collimating hole sets 21 may be aligned with different second collimating hole sets 22, thereby further increasing a diversity of the shapes and sizes of the radiation field.

For example, as shown in FIG. 6, the first collimating portion 11 includes four first collimating hole sets 21, which are arranged in four rows, including the first first collimating hole set 211, the second first collimating hole set 212, the third first collimating hole set 213 and the fourth first collimating hole set 214. Each first collimating hole set 21 includes three first collimating holes 23, the aperture sizes of the three first collimating holes 23 in a same set are the same, and the aperture sizes of the four first collimating hole sets 21 are different (in this case, the aperture size of the first collimating hole set 21 is equal to an aperture size of each first collimating hole 23 in the set). The aperture size of the first first collimating hole set 211 may be the largest, the aperture size of the third first collimating hole set 213 may be set as the smallest, and the aperture size of the second first collimating hole set 212 may be set as greater than the aperture size of the third first collimating hole set 213 but less than the aperture size of the fourth first collimating hole set 214. The second collimating portion 12 includes four second collimating hole sets 22, and the four second collimating hole sets 22 are arranged in four rows, including the first second collimating hole set 221, the second second collimating hole set 222, the third second collimating hole set 223 and the fourth second collimating hole set 224. Each second collimating hole set includes three second collimating holes, aperture sizes of the three second collimating holes 24 in a same set are the same, and the aperture sizes of the four second collimating hole sets 22 are different (in this case, the aperture size of the second collimating hole set 22 is equal to an aperture size of each first collimating hole 24 in the set). The aperture size of the first second collimating hole set 221 may be set as the largest, the aperture size of the third second collimating hole set 223 may be set as the smallest, and the aperture size of the second second collimating hole set 222 may be set as greater than the aperture size of the third second collimating hole set 223 but less than the aperture size of the fourth second collimating hole set 224.

In this way, in a case where relative positions of the first collimating portion 11 and the second collimating portion 12 are adjusted, the first first collimating hole set 211 may be aligned with the first second collimating hole set 221, or may also be aligned with the second second collimating hole set 222, or may also be aligned with the third second collimating hole set 223, or may also be aligned with the fourth second collimating hole set 224. The second first collimating hole set 212 may be aligned with the first second collimating hole set 221, or may also be aligned with the second second collimating hole set 222, or may also be aligned with the third second collimating hole set 223, or may also be aligned with the fourth second collimating hole set 224. Alignments of the third first collimating hole set 213 and the fourth first collimating hole set 214 with each second collimating hole set 22 are similar. Since the aperture sizes of the four first collimating hole sets 21 are not completely equal to each other, and the aperture sizes of the four second collimating hole sets 22 are not completely equal to each other, different first collimating hole sets 21 may be aligned with different second collimating hole sets 22 by adjusting the relative positions of the first collimating portion 11 and the second collimating portion 12 to obtain more various shapes of the radiation field, which may meet needs of different occasions and increase application range of products.

Of course, in the embodiment, other numbers of the first collimating hole sets may be provided, such as two or three or five or more first collimating hole sets. Aperture sizes of the plurality of first collimating hole sets may also be the same in two sets, or aperture sizes of first collimating holes in a certain collimating hole set may be different. In the embodiment, other numbers of the second collimating hole sets may be provided, such as two or three or five or more second collimating hole sets. Aperture sizes of the plurality of second collimating hole sets may also be the same in two sets, or aperture sizes of the second collimating holes in a certain collimating hole set may be different.

In this embodiment, the number of the first collimating hole sets and the number of the second collimating hole sets may be the same or different, for example, the above four first collimating hole sets and four second collimating hole sets may also be set as three first collimating hole sets and five second collimating hole sets, or other numbers of first collimating hole sets and other numbers of second collimating hole sets, or the like.

In the present embodiment, the number of the first collimating holes in any one of the first collimating hole sets is not limited, and the number of the second collimating holes in any one of the second collimating hole sets is also not limited. The number of the first collimating holes in any one of the collimating hole sets and the number of the second collimating holes in any one of the second collimating hole sets may be same or different, for example, there are three first collimating holes in one of the first collimating hole sets, and three second collimating holes in one of the second collimating hole sets. Of course, there may be four first collimating holes in one of the first collimating hole sets, and three or five or other numbers of the second collimating holes in one of the second collimating hole sets.

Exemplified in this embodiment, the number of the first collimating hole sets included in the first collimating portion is equal to the number of the second collimating hole sets included in the second collimating portion. In this way, in a case where the first collimating portion and the second collimating portion are adjusted, it is more convenient to align the first collimating hole sets and the second collimating hole sets, and align different first collimating hole sets and different second collimating hole sets, thereby conveniently and quickly switching the shapes and sizes of the radiation field. For example, as shown in FIG. 6, the first collimating portion 11 includes four first collimating hole sets 21, and the second collimating portion includes four second collimating hole sets 22, and of course, other numbers of the first collimating hole sets 21 and the second collimating hole sets 22 may also be set, such as one, two or three or five first collimating hole sets 21 and second collimating hole sets 22.

Exemplified in this embodiment, each first collimating hole set may have one or two or more first collimating holes. In a case where there are a plurality of first collimating holes, aperture sizes of the plurality of first collimating holes may be the same or different. As shown in FIG. 6, aperture sizes of the plurality of first collimating holes 23 may be the same in the embodiment. Aperture sizes of three first collimating holes 23 in the first first collimating hole sets 211 are the same, aperture sizes of three first collimating holes 23 in the second first collimating hole sets 212 are the same, aperture sizes of three first collimating holes 23 in the third first collimating hole sets 213 are the same, and aperture sizes of three first collimating holes 23 in the fourth first collimating hole sets 214 are the same. However, aperture sizes of the first collimating holes 23 in the first first collimating hole sets may be the same as or different from aperture sizes of the first collimating holes 23 in the second first collimating hole sets, aperture sizes of the first collimating holes in the third first collimating hole sets, and aperture sizes of the first collimating holes in the fourth first collimating hole sets. In this embodiment, an aperture size of each first collimating hole in each first collimating hole set may be selected to be different to increase the diversity of the shapes and sizes of the radiation field.

For example, each second collimating hole set may have one or two or more second collimating holes. In a case where there are a plurality of second collimating holes, aperture sizes of the plurality of second collimating holes may be the same or different. As shown in FIG. 6, aperture sizes of the plurality of second collimating holes 24 may be the same in the embodiment. Aperture sizes of three second collimating holes in the first second collimating hole set 221 are the same, aperture sizes of three second collimating holes in the second second collimating hole set 222 are the same, aperture sizes of three second collimating holes in the third second collimating hole set 223 are the same, and aperture sizes of three second collimating holes in the fourth second collimating hole set 224 are the same. However, aperture sizes of the second collimating holes in the first second collimating hole sets may be the same as or different from aperture sizes of the second collimating holes in the second second collimating hole sets, aperture sizes of the second collimating holes in the third second collimating hole sets, and aperture sizes of the second collimating holes in the fourth second collimating hole sets. In this embodiment, an aperture size of each second collimating hole in each second collimating hole set may be selected to be different to increase the diversity of the shapes and sizes of the radiation field.

Exemplified in this embodiment, the aperture sizes of the plurality of first collimating hole sets are the same as the aperture sizes of the plurality of second collimating hole sets. For example, as shown in FIG. 6, distribution of the first collimating hole sets 21 and distribution of the second collimating hole sets 22 may be symmetrically arranged, and an axis of symmetry is a straight line segment formed by an intersection of the first collimating portion 11 and the second collimating portion 12. For example, as shown in FIG. 6, the aperture size of the first first collimating hole set 211 in this embodiment is the same as the aperture size of the first second collimating hole set 221, the aperture size of the second first collimating hole set 212 is the same as the aperture size of the second second collimating hole set 222, the aperture size of the third first collimating hole set 213 is the same as the aperture sizes of the third second collimating hole set 223, and the aperture size of the fourth first collimating hole set 214 is the same as the aperture size of the fourth second collimating hole set 224. Of course, in the embodiment, other numbers of the first collimating hole sets and second collimating hole sets may be set, such as two or three or five or six first collimating hole sets and second collimating hole sets.

Exemplified in the embodiment, as shown in FIG. 1, the collimating body includes a first driving portion 31, and the first driving portion 31 drives the first collimating portion 11 to move in the direction perpendicular to the side-by-side direction relative to the second collimating portion 12, so as to adjust the relative positions of the first collimating portion 11 and the second collimating portion 12 in the direction perpendicular to the side-by-side direction to align or stagger the first collimating hole sets 21 and the second collimating hole sets 22. Power sources of the first driving portion 31 may adopt motor drive, aerodynamic drive, hydraulic drive and the like. A driving connection portion of the first driving portion may be connected to the power source and the first collimating portion by adopting a telescopic rod, or connected to the power source and the first collimating portion by a gear unit, or connected power source and the first collimating portion by a worm and gear, or connected to the power source and the first collimating portion by a ball screw, or connected to the power source and the first collimating portion by a polished rod slider, or the like. As shown in FIG. 1, a transmission mode may be realized by a motor driven ball screw in this embodiment. The first driving portion 31 includes a first motor 41, and an output shaft of the first motor 41 is connected to a first lead screw 42. The first collimating portion 11 is mounted on the first lead screw 42 to drive a movement of the first collimating portion 11 as the first lead screw 42 rotates.

In this embodiment, the collimating body further includes a first brake portion, and the first brake portion is configured to limit a movement of the first drive portion. In this way, during the treatment, a deflection of the first collimating portion due to factors such as gravity may be prevented in a case where the therapy head is deflected to an angle, and the first brake portion is adopted to keep the first collimating portion stationary, not deflected. The first brake portion may be a brake mounted on the power output shaft, or a brake restricting the movement of the first collimating portion, or a brake mounted on the motor shaft in this embodiment.

Exemplified in the embodiment, as shown in FIG. 1, the collimating body further includes a second driving portion 32, and the second driving portion 32 drives the second collimating portion 12 to move in the direction perpendicular to the side-by-side direction relative to the first collimating portion 11. In this way, the second collimating portion 12 may be driven to move, so as to adjust the relative positions of the second collimating portion 12 and the first collimating portion 11 in the direction perpendicular to the side-by-side direction to align or stagger the first collimating hole sets 21 and the second collimating hole sets 22. Power sources of the second driving portion 32 may adopt motor drive, aerodynamic drive, hydraulic drive and the like. A driving connection portion of the second driving portion may be connected to the power source and the second collimating portion by adopting a telescopic rod, or connected to the power source and the second collimating portion by a gear unit, or connected power source and the second collimating portion by a worm and gear, or connected to the power source and the second collimating portion by a ball screw, or connected to the power source and the second collimating portion by a polished rod slider, or the like. As shown in FIG. 1, a transmission mode may be realized by a motor driven ball screw in this embodiment. The second driving portion 32 includes a second motor 43, and an output shaft of the second motor 43 is connected to the second lead screw 44. The second collimating portion 12 is mounted on the second lead screw 44 to drive a movement of the second collimating portion 12 as the lead screw rotates. The embodiment may provide only the first driving portion or only the second driving portion, or both the first driving portion and the second driving portion, which may all realize a relative movement of the first collimating portion and the second collimating portion in the direction perpendicular to the side-by-side direction.

In this embodiment, the collimating body further includes a second brake portion, and the second brake portion is configured to limit a movement of the second driving portion. In this way, during the treatment, a deflection of the second collimating portion due to factors such as gravity may be prevented in a case where the therapy head is deflected to an angle, and the second brake portion is adopted to keep the second collimating portion stationary, not deflected. The second brake portion may be a brake mounted on the power output shaft, or a brake restricting the movement of the second collimating portion, or a brake mounted on the motor shaft in this embodiment.

Figure 7:
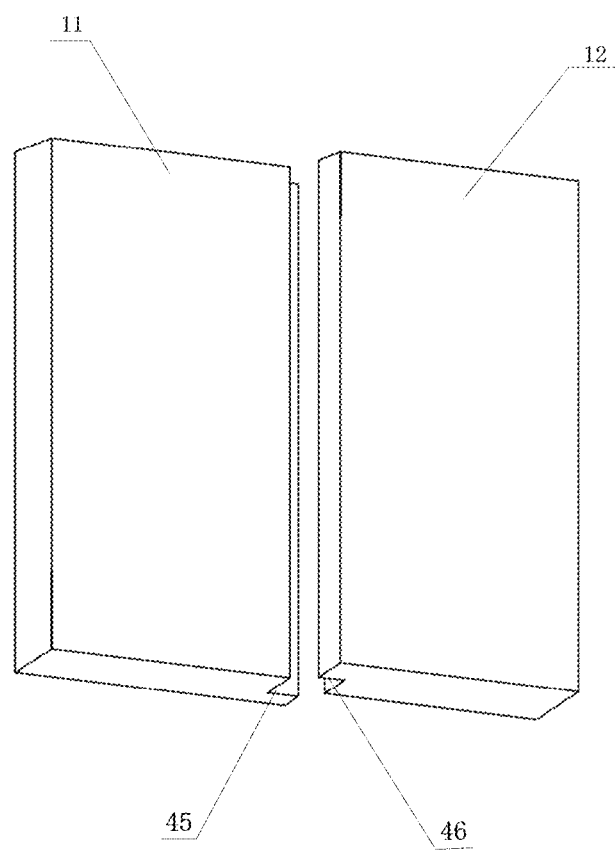
FIG. 7 is an exploded diagram of a collimating body, according to some embodiments of the present disclosure.

Exemplified in this embodiment, as shown in FIG. 7, the first collimating portion 11 includes a first stepped portion 45, and the second collimating portion 12 correspondingly includes a second stepped portion 46 that cooperates with the first stepped portion 45. In this way, a shape of a fitting surface of the first collimating portion 11 and the second collimating portion 12 is a complementary stepped shape to ensure a close fit between the first collimating portion 11 and the second collimating portion 12 to prevent radiation leakage. In the embodiment, the first collimating portion 11 and the second collimating portion 12 may also respectively include two or more stepped portions. For example, the first collimating portion 11 includes two or more stepped portions, and the second collimating portion 12 correspondingly includes two or more stepped portions.

The embodiment is not limited to the above descriptions. For example, the first collimating portion and the second collimating portion may also have other shapes. In the embodiment, shapes of the first collimating portion and the second collimating portion are not limited. In the embodiment, a combination of the collimating hole sets having different aperture sizes may be realized by adopting the relative movement between the first collimating portion and the second collimating portion, thereby not only achieving adjustment of different shapes of the radiation field at the focus, but also increasing the dose control range at the focus and improving the accuracy of the dose control.

A multi-source focusing radiation therapy head is disclosed in the embodiment, including any one of the above collimating bodies. For example, in the embodiment, in a case where the shapes of the radiation field or a dose rate at the focus needs to be adjusted, a servo motor is started to drive the ball screw feed, and the relative movement between the first collimating portion and the second collimating portion is driven by the ball screw. In a case where a target collimating hole set on the first collimating portion is aligned with a target collimating hole set on the second collimating portion, the servo motor is turned off and the brake is kept in a braking state before the treatment may be started.

The above is a further detailed description of the present disclosure in combination with the specific preferred embodiments, and it cannot be assumed that the specific embodiments of the present disclosure are limited to these descriptions. For an ordinary person skilled in the art to which the present disclosure pertains, a number of simple deductions or substitutions may be made without departing from the spirit, which will be considered as belonging to the protection scope of the present disclosure.

What is claimed is:

1. A collimating body, comprising:
a first collimating portion, wherein the first collimating portion includes at least one first collimating hole set; and
a second collimating portion, wherein the second collimating portion includes a plurality of second collimating hole sets;
wherein the first collimating portion and the second collimating portion are arranged side by side in a side-by-side direction and closely fitted; and the first collimating portion and the second collimating portion are able to move oppositely in a direction perpendicular to the side-by-side direction, so as to align or stagger the at least one first collimating hole set and a second collimating hole set of the plurality of second collimating hole sets;
the plurality of second collimating hole sets are distributed in the direction perpendicular to the side-by-side direction;
at least one of the plurality of second collimating hole sets is configured in a way that an aperture size of each second collimating hole in the at least one of the plurality of second collimating hole sets is not equal to an aperture size of each second collimating hole in other second collimating hole sets of the plurality of second collimating hole sets; and
each first collimating hole and each second collimating hole do not overlap in a direction in which a ray beam passes.

2. The collimating body according to claim 1, wherein the at least one first collimating hole set includes a plurality of first collimating hole sets, and the plurality of first collimating hole sets are distributed in the direction perpendicular to the side-by-side direction; and
at least one of the plurality of first collimating hole sets is configured in a way that an aperture size of each first collimating hole in the at least one of the plurality of first collimating hole sets is not equal to an aperture size of each first collimating hole in other first collimating hole sets of the plurality of first collimating hole sets.

3. The collimating body according to claim 1, wherein the at least one first collimating hole set includes a plurality of first collimating hole sets, and an aperture size of each of the plurality of first collimating hole sets is not equal to each other; and
an aperture size of each of the plurality of second collimating hole sets not equal to each other.

4. The collimating body according to claim 3, wherein the number of the first collimating hole sets included in the plurality of first collimating hole sets is equal to the number of the second collimating hole sets included in the plurality of second collimating hole sets.

5. The collimating body according to claim 3, wherein the number of the first collimating holes included in each first collimating hole set of the plurality of first collimating hole sets is equal to the number of the second collimating holes included in each second collimating hole set of the plurality of second collimating hole sets.

6. The collimating body according to claim 3, wherein the number of the first collimating holes included in each first collimating hole set of the plurality of first collimating hole sets is different from the number of the second collimating holes included in each second collimating hole set of the plurality of second collimating hole sets.

7. The collimating body according to claim 1, wherein the at least one first collimating hole set includes a plurality of first collimating holes having a same aperture size, and the plurality of second collimating holes have a same aperture size.

8. The collimating body according to claim 7, wherein the at least one first collimating hole set includes a plurality of first collimating hole sets; and
an aperture size of each of the plurality of first collimating hole sets is equal to an aperture size of each of the plurality of second collimating hole sets in one-to-one correspondence.

9. The collimating body according to claim 1, further comprising a first driving portion, and the first driving portion being configured to drive the first collimating portion to move in the direction perpendicular to the side-by-side direction relative to the second collimating portion.

10. The collimating body according to claim 9, further comprising a first brake portion, and the first brake portion being configured to limit a movement of the first driving portion.

11. The collimating body according to claim 10, further comprising a second driving portion, and the second driving portion being configured to drive the second collimating portion to move in the direction perpendicular to the side-by-side direction relative to the first collimating portion.

12. The collimating body according to claim 11, further comprising a second brake portion, and the second brake portion being configured to limit a movement of the second driving portion.

13. The collimating body according to claim 1, wherein the first collimating portion includes a first stepped portion; and
the second collimating portion includes a second stepped portion that cooperates with the first stepped portion.

14. The collimating body according to claim 1, wherein the at least one first collimating hole set includes a plurality of first collimating holes with aperture sizes which are not equal to each other, and the second collimating hole set of the plurality of second collimating hole sets includes a plurality of second collimating holes with aperture sizes which are not equal to each other.

15. A multi-source focusing radiation therapy head, comprising the collimating body according to claim 1.

* * * * *